(12) United States Patent
Ishizawa et al.

(10) Patent No.: US 10,426,386 B2
(45) Date of Patent: Oct. 1, 2019

(54) NON-INVASIVE BLOOD GLUCOSE LEVEL MEASUREMENT METHOD AND NON-INVASIVE BLOOD GLUCOSE LEVEL MEASUREMENT DEVICE

(71) Applicant: Shinshu University, Matsumoto-shi, Nagano (JP)

(72) Inventors: Hiroaki Ishizawa, Ueda (JP); Shouhei Koyama, Ueda (JP)

(73) Assignee: SHINSHU UNIVERSITY, Matsumoto-shi, Nagano (JP)

( * ) Notice: Subject to any disclaimer, the term of this patent is extended or adjusted under 35 U.S.C. 154(b) by 121 days.

(21) Appl. No.: 15/544,677

(22) PCT Filed: Feb. 19, 2016

(86) PCT No.: PCT/JP2016/054893
§ 371 (c)(1),
(2) Date: Jul. 19, 2017

(87) PCT Pub. No.: WO2016/147795
PCT Pub. Date: Sep. 22, 2016

(65) Prior Publication Data
US 2018/0008175 A1    Jan. 11, 2018

(30) Foreign Application Priority Data

Mar. 13, 2015  (JP) ................................ 2015-051252

(51) Int. Cl.
*A61B 5/00* (2006.01)
*A61B 5/145* (2006.01)
(Continued)

(52) U.S. Cl.
CPC ............ *A61B 5/14532* (2013.01); *A61B 5/02* (2013.01); *A61B 5/02416* (2013.01);
(Continued)

(58) Field of Classification Search
CPC .............. A61B 5/1455; A61B 5/14532; A61B 5/02416; A61B 5/7278
See application file for complete search history.

(56) References Cited

U.S. PATENT DOCUMENTS

2002/0072860 A1* 6/2002 Amano ............... A61B 5/02007
702/19
2011/0245637 A1* 10/2011 McKenna ........... A61B 5/14552
600/310

FOREIGN PATENT DOCUMENTS

| JP | 2004-113434 A | 4/2004 |
| JP | 2009-233284 A | 10/2009 |
| JP | 2012-191969 A | 10/2012 |

OTHER PUBLICATIONS

International Search Report for PCT/JP2016/054893 (1 page).
(Continued)

*Primary Examiner* — Christian Jang
(74) *Attorney, Agent, or Firm* — Flynn Thiel, P.C.

(57) ABSTRACT

A non-invasive blood glucose level measurement device (1) is provided with a pulse waveform measurement unit (2) having FBG sensors (4) for measuring an acceleration pulse wave of a test subject; and a data-processing unit (3) for calculating the blood glucose level of the test subject at the point in time of measurement of the acceleration pulse wave, from waveform information of the measured acceleration pulse wave, on the basis of a predetermined correlation. The correlation is a calibration curve constructed by carrying out a PLS regression analysis, using the blood glucose level measured by a non-invasive blood glucose method as the objective variable, and a simultaneously-measured acceleration pulse wave as the explanatory variable. A non-invasive blood glucose level measurement device capable of mea- (Continued)

suring a blood glucose level at about the same measurement accuracy as an invasive blood glucose measurement device can be achieved thereby.

8 Claims, 31 Drawing Sheets

(51) Int. Cl.
    *A61B 5/02*          (2006.01)
    *A61B 5/1455*      (2006.01)
    *A61B 5/024*       (2006.01)
    *A61B 5/1495*      (2006.01)
(52) U.S. Cl.
    CPC .......... *A61B 5/1455* (2013.01); *A61B 5/1495* (2013.01); *A61B 5/7246* (2013.01); *A61B 5/7278* (2013.01)

(56) References Cited

OTHER PUBLICATIONS

Clinical Assessment of Accelerated Plethysmography in Patients with Diabetes Mellitus, by Norio Kase, Journal of the Japan Diabetic Society, 1989, vol. 32, No. 4, pp. 229-236.

\* cited by examiner

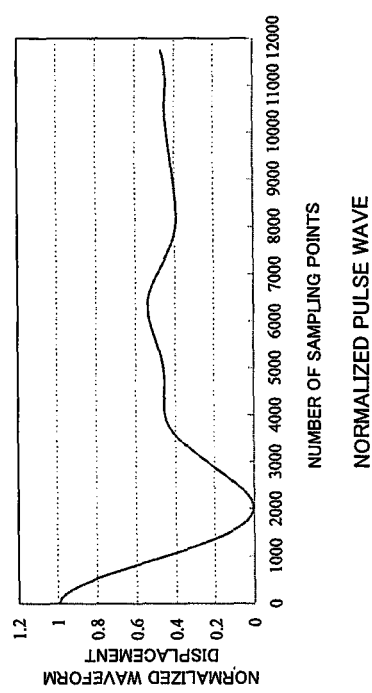
FIG. 2.1

CALIBRATION CURVE CONSTRUCTION AND VALIDATION RESULTS

| NUMBER OF CONSTRUCTION POINTS | AVERAGE VALUE | MINIMUM VALUE | MAXIMUM VALUE |
|---|---|---|---|
| 60 | 122 | 80 | 178 |
| PLS RESULTS | FACTOR NUMBER | CORRELATION COEFFICIENT | SEC[mg/dl] |
| | 4 | 0.69 | 18 |

| NUMBER OF VALIDATION POINTS | AVERAGE VALUE | MINIMUM VALUE | MAXIMUM VALUE |
|---|---|---|---|
| 20 | 114 | 81 | 173 |
| PLS RESULTS | SEP[mg/dl] | | |
| | 23 | | |
| EGA RESULTS | A zone | 65.0%(13/20) | |
| | B zone | 35.0%(7/20) | |

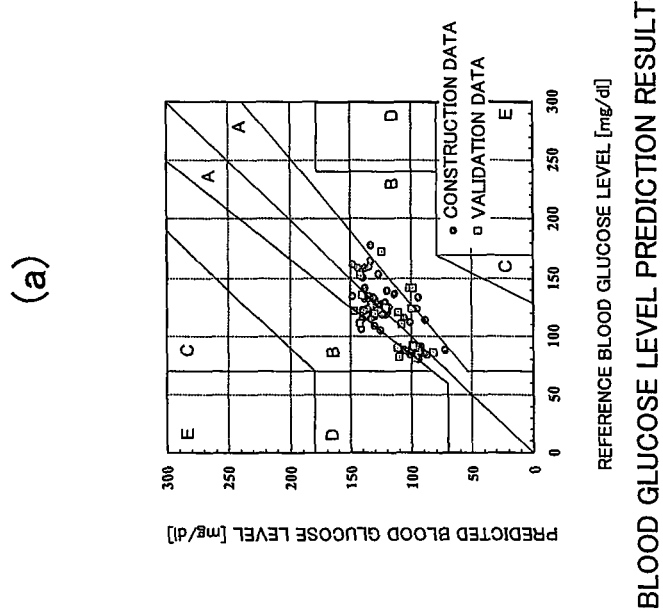

(a)

BLOOD GLUCOSE LEVEL PREDICTION RESULTS

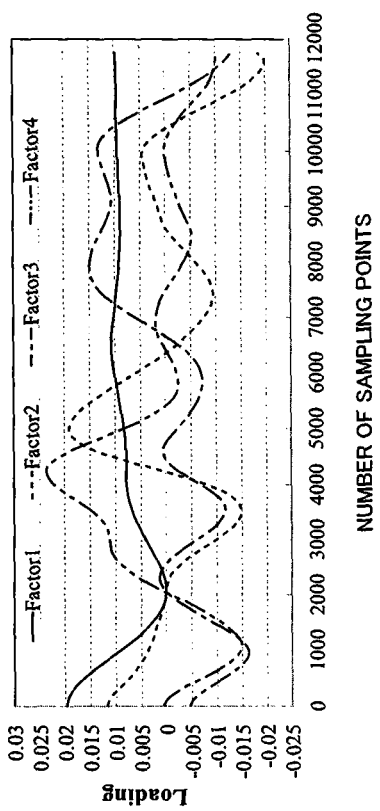
FIG. 2.3

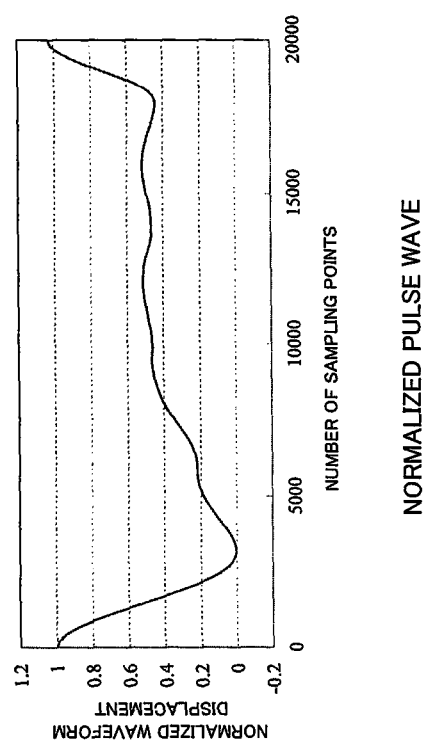
FIG. 2.4

FIG. 2.5

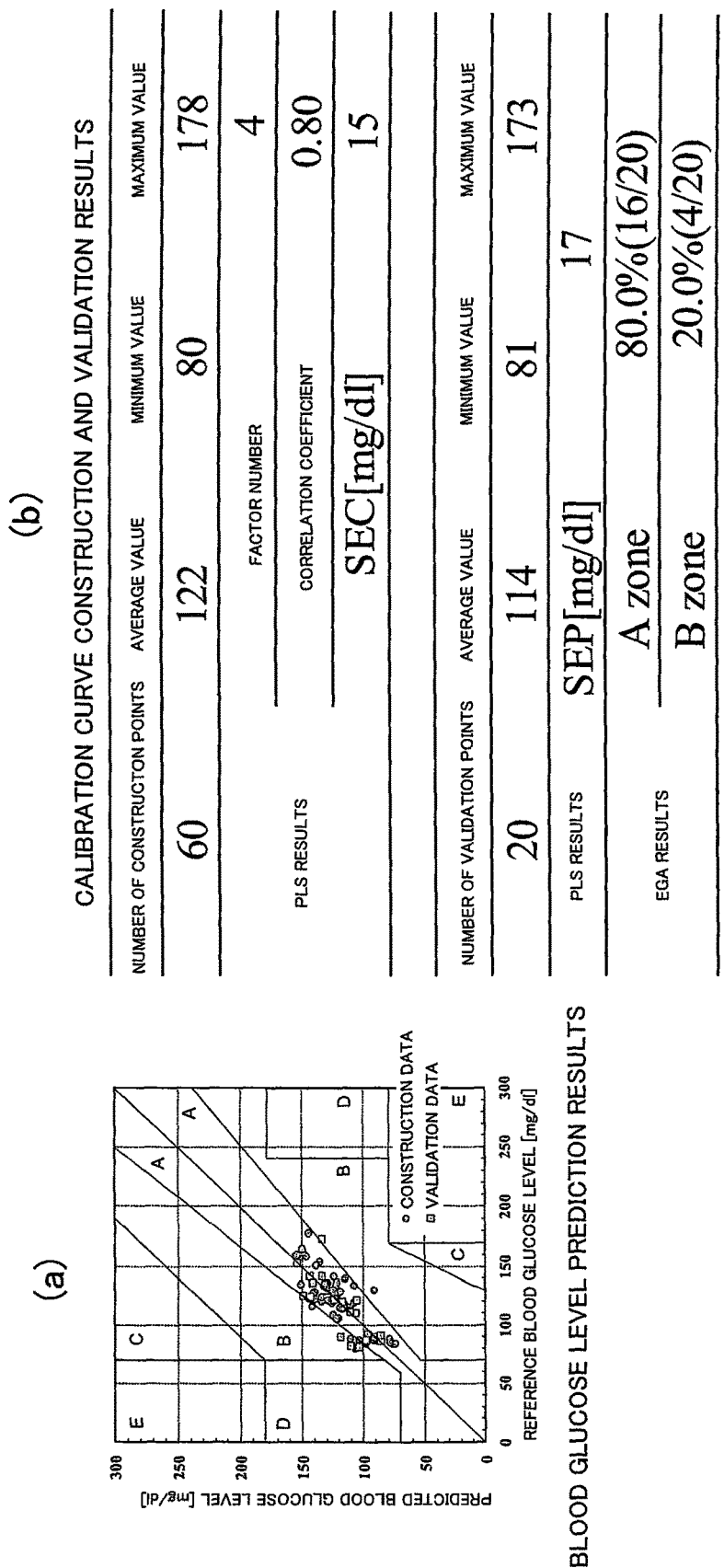

(a) BLOOD GLUCOSE LEVEL PREDICTION RESULTS (b) CALIBRATION CURVE CONSTRUCTION AND VALIDATION RESULTS

| NUMBER OF CONSTRUCTION POINTS | AVERAGE VALUE | MINIMUM VALUE | MAXIMUM VALUE |
|---|---|---|---|
| 60 | 122 | 80 | 178 |
| PLS RESULTS | FACTOR NUMBER | | 4 |
| | CORRELATION COEFFICIENT | | 0.80 |
| | SEC[mg/dl] | | 15 |

| NUMBER OF VALIDATION POINTS | AVERAGE VALUE | MINIMUM VALUE | MAXIMUM VALUE |
|---|---|---|---|
| 20 | 114 | 81 | 173 |
| PLS RESULTS | SEP[mg/dl] | | 17 |
| EGA RESULTS | A zone | | 80.0%(16/20) |
| | B zone | | 20.0%(4/20) |

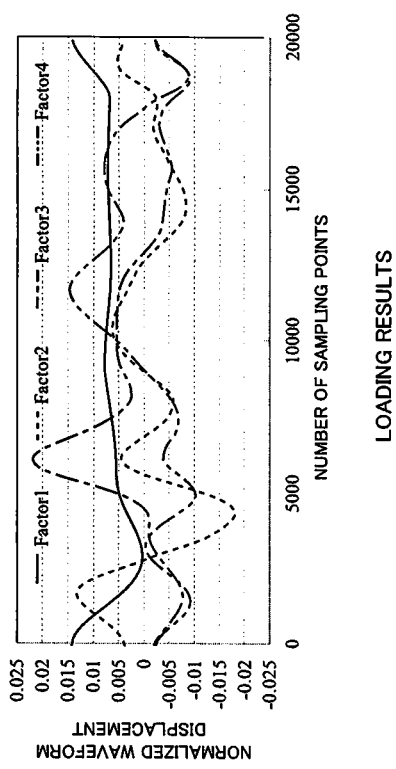
FIG. 2.6

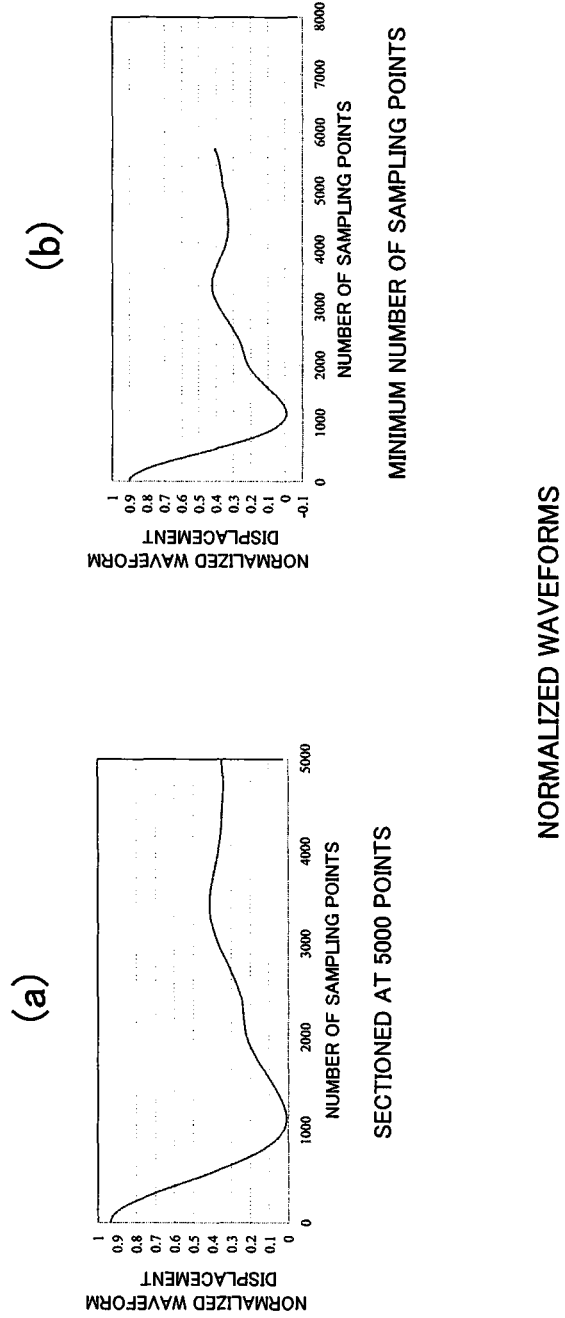
FIG. 3.1

FIG. 3.2
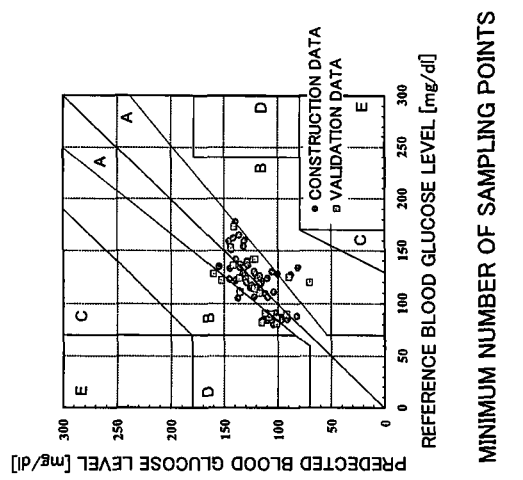
BLOOD GLUCOSE LEVEL PREDICTION RESULTS

FIG. 3.3

CALIBRATION CURVE CONSTRUCTION AND VALIDATION RESULTS (a) SECTIONED AT 5000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | FACTOR NUMBER | | | 4 |
| | CORRELATION COEFFICIENT | | | 0.67 |
| | SEC [mg/dl] | | | 18 |

| | NUMBER OF VALIDATION POINTS | AVERAGE VALUE | MINIMUM VALUE | MAXIMUM VALUE |
|---|---|---|---|---|
| | 20 | 115 | 81 | 173 |
| PLS RESULTS | SEP [mg/dl] | | | 25 |
| EGA RESULTS | A zone | | | 65.0% (9/20) |
| | B zone | | | 45.0% (11/20) |

(b) MINIMUM NUMBER OF SAMPLING POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | FACTOR NUMBER | | | 4 |
| | CORRELATION COEFFICIENT | | | 0.65 |
| | SEC [mg/dl] | | | 18 |

| | NUMBER OF VALIDATION POINTS | AVERAGE VALUE | MINIMUM VALUE | MAXIMUM VALUE |
|---|---|---|---|---|
| | 20 | 115 | 81 | 173 |
| PLS RESULTS | SEP [mg/dl] | | | 25 |
| EGA RESULTS | A zone | | | 55.0% (11/20) |
| | B zone | | | 45.0% (9/20) |

FIG. 3.4
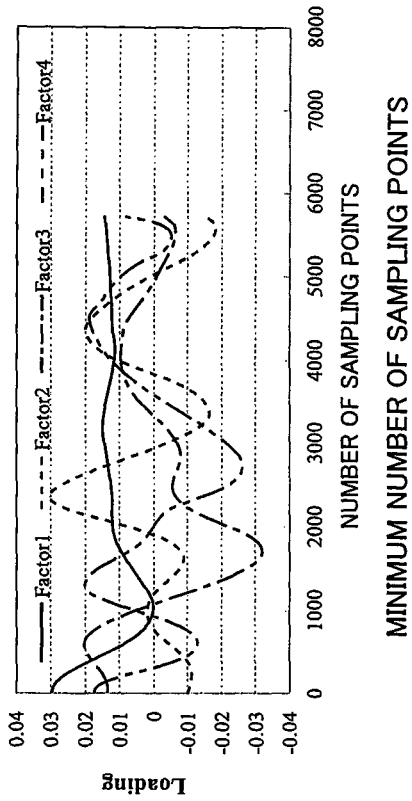
(a) SECTIONED AT 5000 POINTS
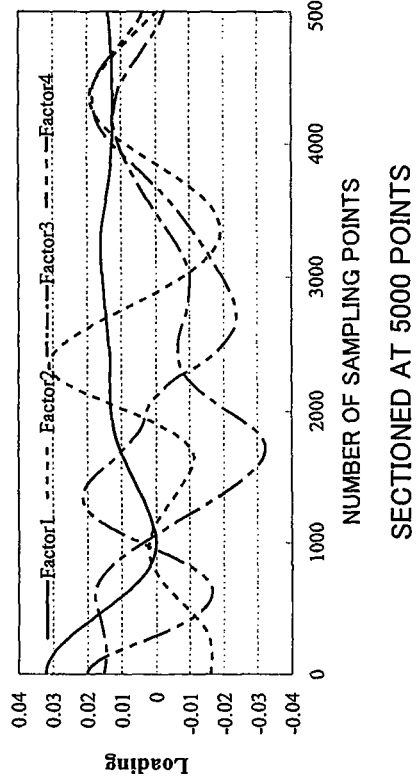
(b) MINIMUM NUMBER OF SAMPLING POINTS
LOADING RESULTS FIG. 3.5
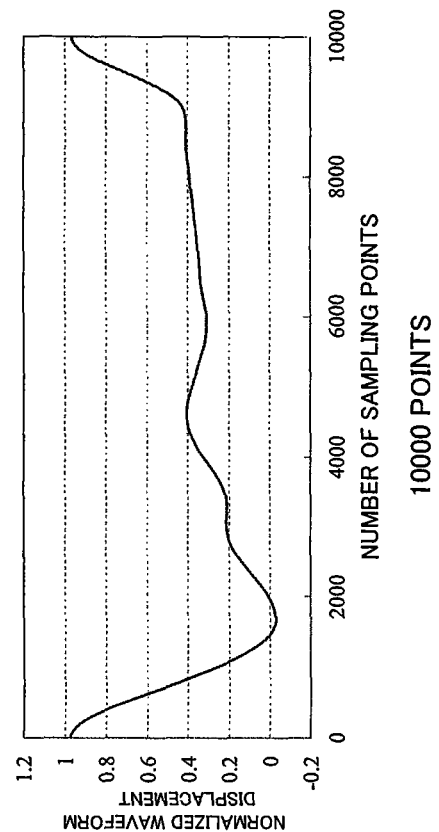
(b)
10000 POINTS
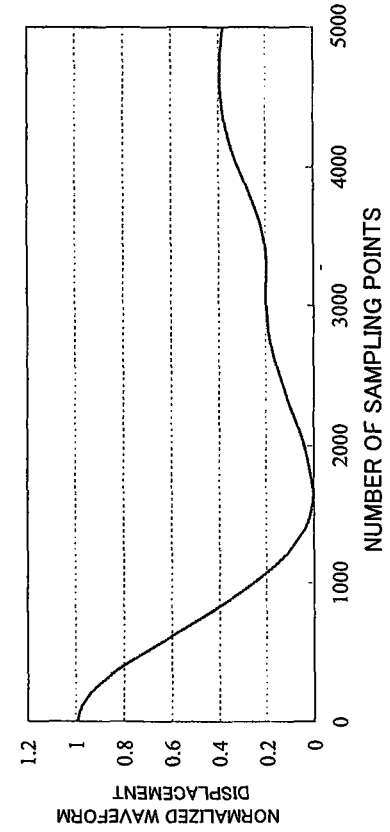
(a)
SECTIONED AT 5000 POINTS
NORMALIZED PULSE WAVEFORMS FIG. 3.6
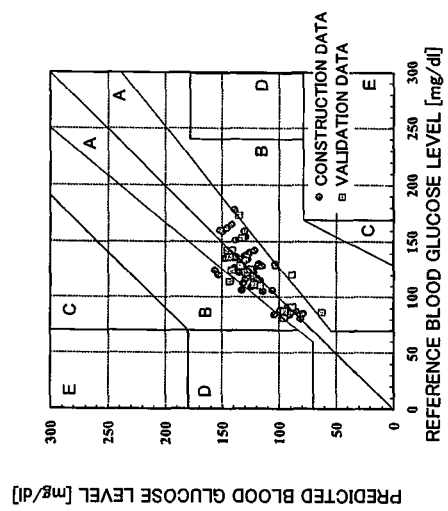
(a)
SECTIONED AT 5000 POINTS
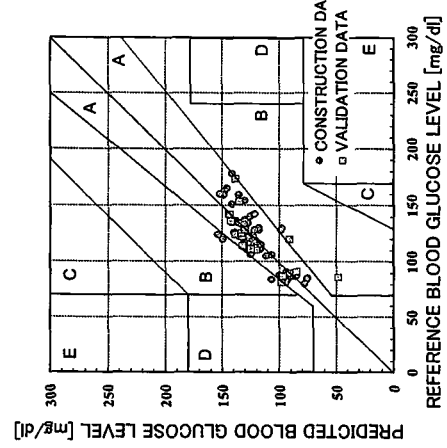
(b)
10000 POINTS
BLOOD GLUCOSE LEVEL PREDICTION RESULTS

FIG. 3.7

CALIBRATION CURVE CONSTRUCTION AND VALIDATION RESULTS (a) SECTIONED AT 5000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | | FACTOR NUMBER | CORRELATION COEFFICIENT | 0.81 |
| | | | | 4 |
| | | SEC[mg/dl] | | 14 |

| | NUMBER OF VALIDATION POINTS | AVERAGE VALUE | MINIMUM VALUE | MAXIMUM VALUE |
|---|---|---|---|---|
| | 20 | 115 | 81 | 173 |
| PLS RESULTS | SEP[mg/dl] | | | 17 |
| EGA RESULTS | A zone | | | 85.0%(17/20) |
| | B zone | | | 15.0%(3/20) |

(b) 10000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | | FACTOR NUMBER | CORRELATION COEFFICIENT | 0.79 |
| | | | | 4 |
| | | SEC[mg/dl] | | 15 |

| | NUMBER OF VALIDATION POINTS | AVERAGE VALUE | MINIMUM VALUE | MAXIMUM VALUE |
|---|---|---|---|---|
| | 20 | 115 | 81 | 173 |
| PLS RESULTS | SEP[mg/dl] | | | 17 |
| EGA RESULTS | A zone | | | 80.0%(16/20) |
| | B zone | | | 20.0%(6/20) |

FIG. 3.8
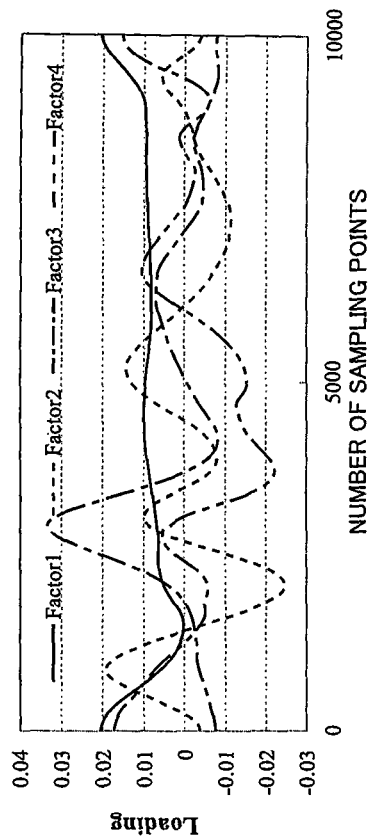
(a) SECTIONED AT 5000 POINTS
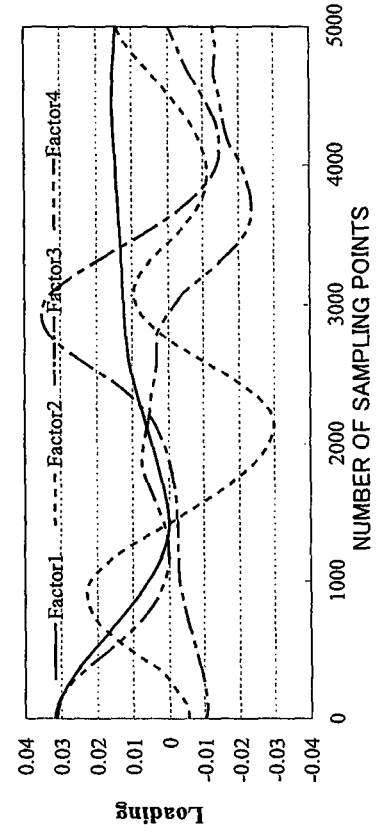
(b) 10000 POINTS
LOADING RESULTS FIG. 4.1
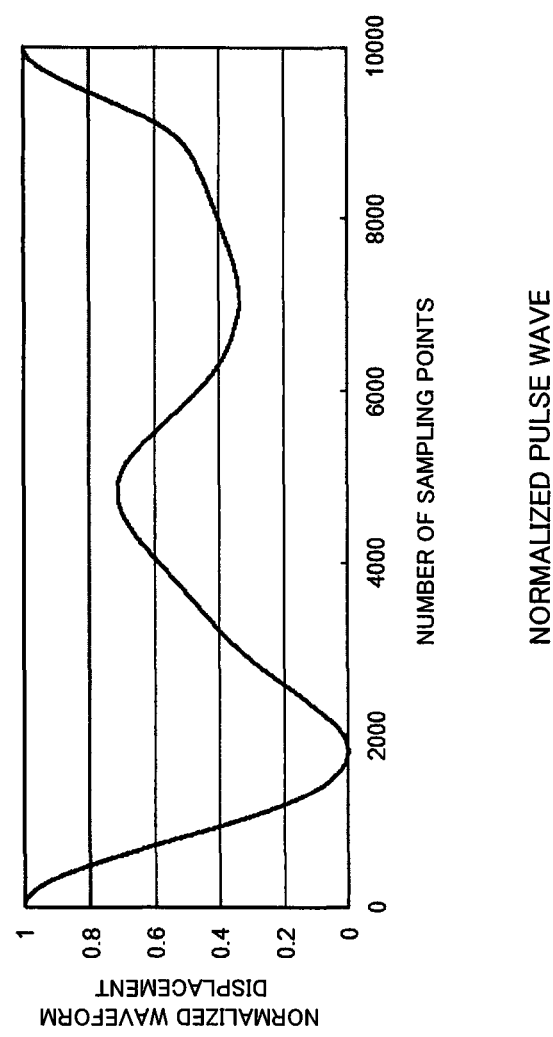

FIG. 4.2
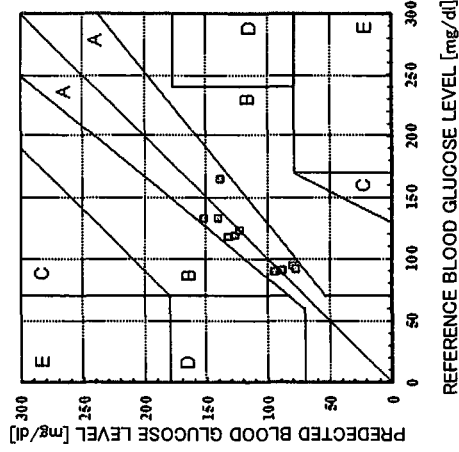
(a) CALIBRATION CURVE CONSTRUCTION RESULTS
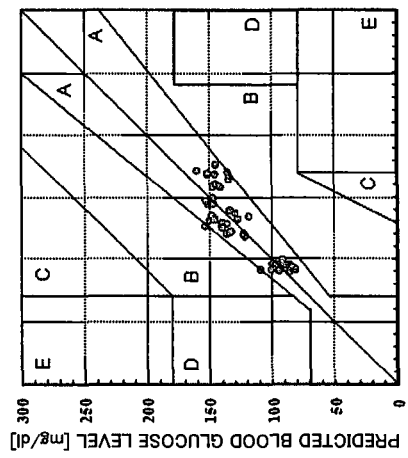
(b) CALIBRATION CURVE VALIDATION RESULTS

FIG. 4.3

CALIBRATION CURVE CONSTRUCTION AND VALIDATION RESULTS

| NUMBER OF CONSTRUCTON POINTS | AVERAGE VALUE | MINIMUM VALUE | MAXIMUM VALUE |
|---|---|---|---|
| 50 | 127 | 89 | 176 |
| PLS RESULTS | FACTOR NUMBER | | 4 |
| | CORRELATION COEFFICIENT | | 0.87 |
| | SEC[mg/dl] | | 14 |

| NUMBER OF VALIDATION POINTS | AVERAGE VALUE | MINIMUM VALUE | MAXIMUM VALUE |
|---|---|---|---|
| 10 | 115 | 89 | 164 |
| PLS RESULTS | SEP[mg/dl] | | 14 |
| EGA RESULTS | A zone | | 100%(10/10) |

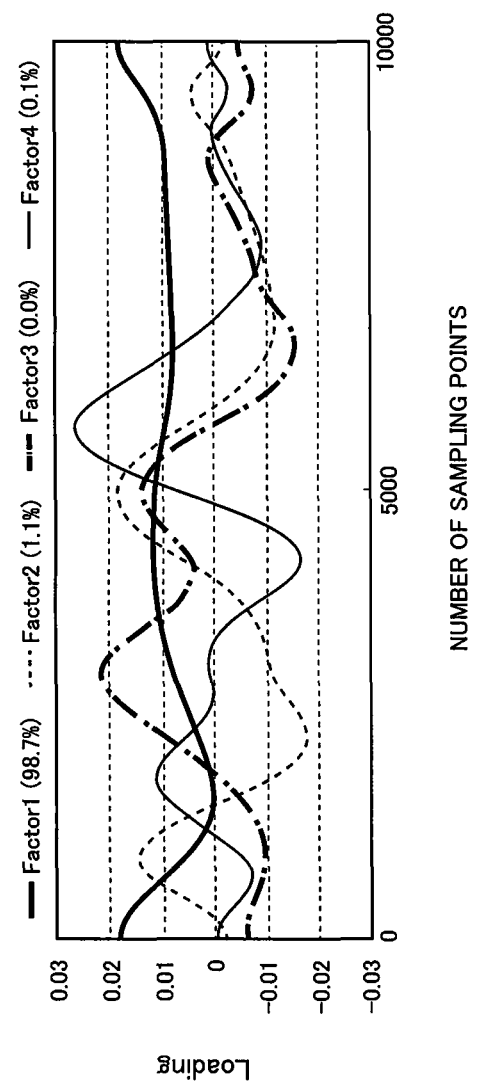
FIG. 4.4

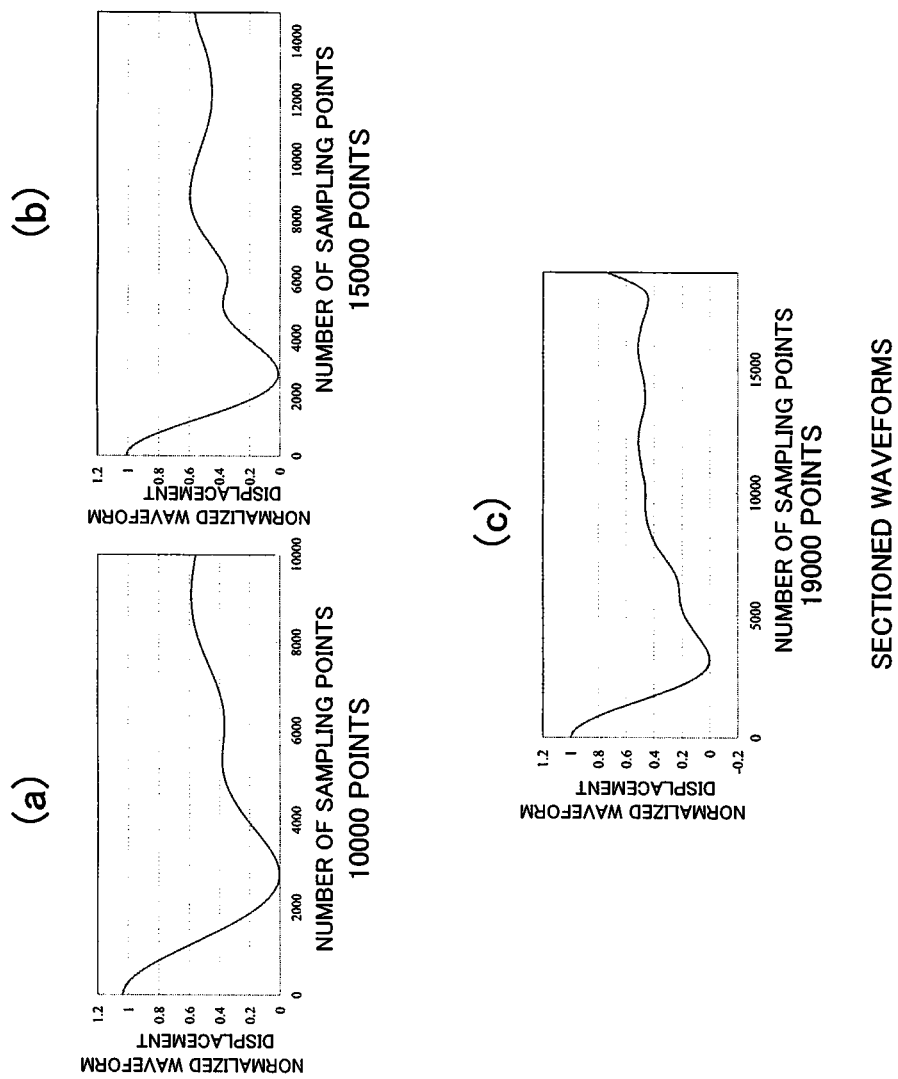

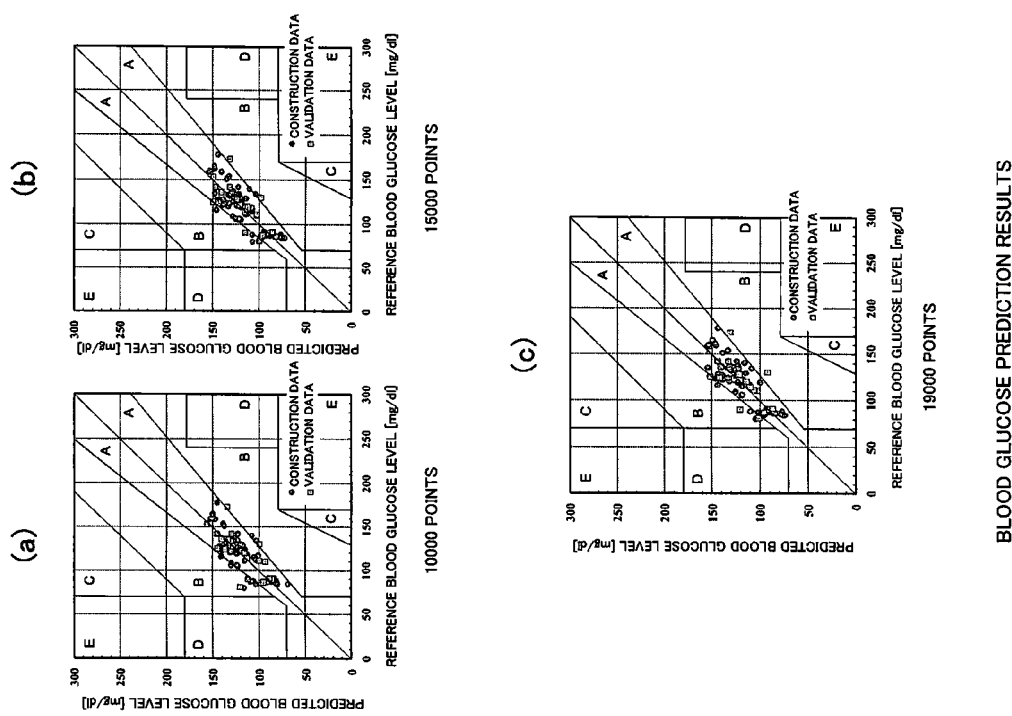

FIG. 5.3
CALIBRATION CURVE CONSTRUCTION AND VALIDATION RESULTS (a) 10000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | | FACTOR NUMBER | | 4 |
| | | CORRELATION COEFFICIENT | | 0.80 |
| | | SEC[mg/dl] | | 15 |

| | NUMBER OF VALIDATION POINTS | AVERAGE VALUE | MINIMUM VALUE | MAXIMUM VALUE |
|---|---|---|---|---|
| | 20 | 118 | 81 | 173 |
| PLS RESULTS | SEP[mg/dl] | | | 17 |
| EGA RESULTS | A zone | | 80.0%(16/20) | |
| | B zone | | 20.0%(4/20) | |

(b) 15000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | | FACTOR NUMBER | | 4 |
| | | CORRELATION COEFFICIENT | | 0.80 |
| | | SEC[mg/dl] | | 15 |

| | NUMBER OF VALIDATION POINTS | AVERAGE VALUE | MINIMUM VALUE | MAXIMUM VALUE |
|---|---|---|---|---|
| | 20 | 118 | 81 | 173 |
| PLS RESULTS | SEP[mg/dl] | | | 17 |
| EGA RESULTS | A zone | | 75.0%(15/20) | |
| | B zone | | 25.0%(5/20) | |

(c) 19000 POINTS

| | NUMBER OF CONSTRUCTION POINTS | AVERAGE VALUE | MINIMUM VALUE | MAXIMUM VALUE |
|---|---|---|---|---|
| | 60 | 122 | 80 | 178 |
| PLS RESULTS | | FACTOR NUMBER | | 4 |
| | | CORRELATION COEFFICIENT | | 0.82 |
| | | SEC[mg/dl] | | 14 |

| | NUMBER OF VALIDATION POINTS | AVERAGE VALUE | MINIMUM VALUE | MAXIMUM VALUE |
|---|---|---|---|---|
| | 20 | 118 | 81 | 173 |
| PLS RESULTS | SEP[mg/dl] | | 18 | |
| EGA RESULTS | A zone | | 75.0%(15/20) | |
| | B zone | | 25.0%(5/20) | |

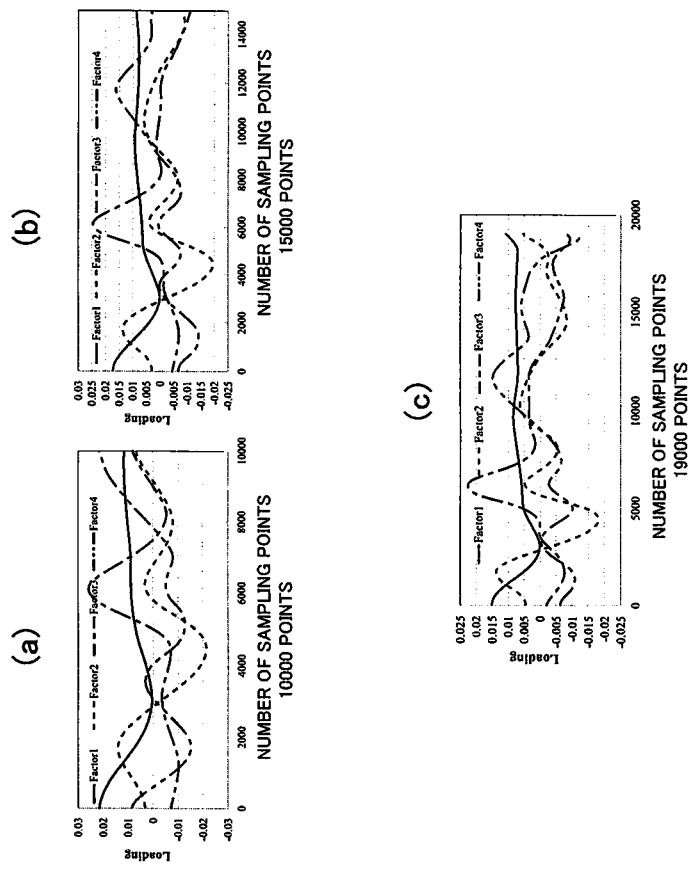
FIG. 5.4
LOADING RESULTS

FIG. 6.1
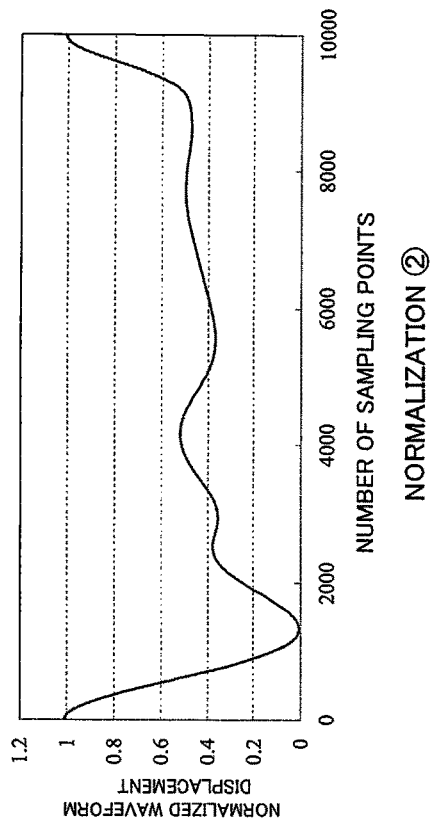
(a) NORMALIZATION ①
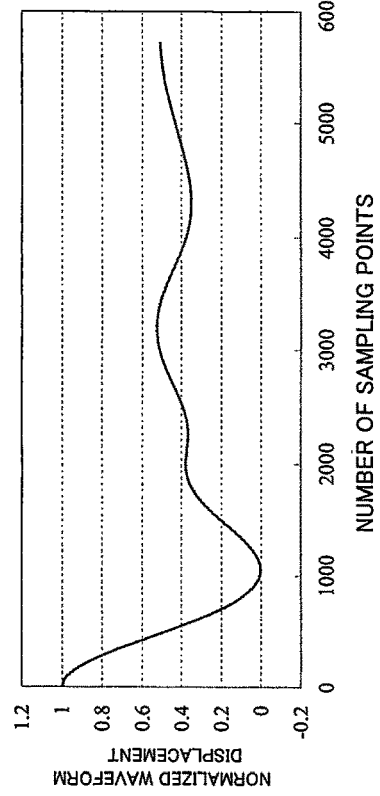
(b) NORMALIZATION ②
NORMALIZED PULSE WAVEFORMS (ELBOW)

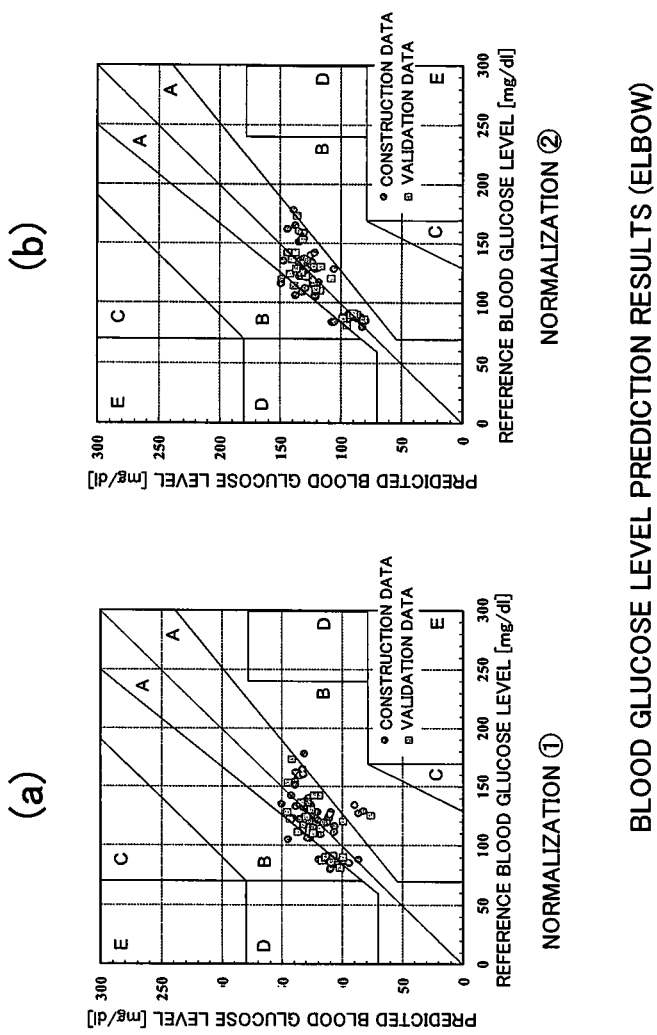
FIG. 6.2

FIG. 6.3

CALIBRATION CURVE CONSTRUCTION AND VALIDATION RESULTS (ELBOW)

(a) NORMALIZATION ①

| NUMBER OF CONSTRUCTION POINTS | AVERAGE VALUE | MINIMUM VALUE | MAXIMUM VALUE |
|---|---|---|---|
| 60 | 122 | 80 | 178 |

| PLS RESULTS | FACTOR NUMBER | CORRELATION COEFFICIENT | SEC[mg/dl] |
|---|---|---|---|
| | 4 | 0.55 | 21 |

| NUMBER OF VALIDATION POINTS | AVERAGE VALUE | MINIMUM VALUE | MAXIMUM VALUE |
|---|---|---|---|
| 20 | 118 | 81 | 173 |

| PLS RESULTS | SEP[mg/dl] | | 22 |
|---|---|---|---|
| EGA RESULTS | A zone | | 70.0%(14/20) |
| | B zone | | 30.0%(6/20) |

(b) NORMALIZATION ②

| NUMBER OF CONSTRUCTION POINTS | AVERAGE VALUE | MINIMUM VALUE | MAXIMUM VALUE |
|---|---|---|---|
| 60 | 122 | 80 | 178 |

| PLS RESULTS | FACTOR NUMBER | CORRELATION COEFFICIENT | SEC[mg/dl] |
|---|---|---|---|
| | 4 | 0.76 | 16 |

| NUMBER OF VALIDATION POINTS | AVERAGE VALUE | MINIMUM VALUE | MAXIMUM VALUE |
|---|---|---|---|
| 20 | 118 | 81 | 173 |

| PLS RESULTS | SEP[mg/dl] | | 14 |
|---|---|---|---|
| EGA RESULTS | A zone | | 90.0%(18/20) |
| | B zone | | 10.0%(2/20) |

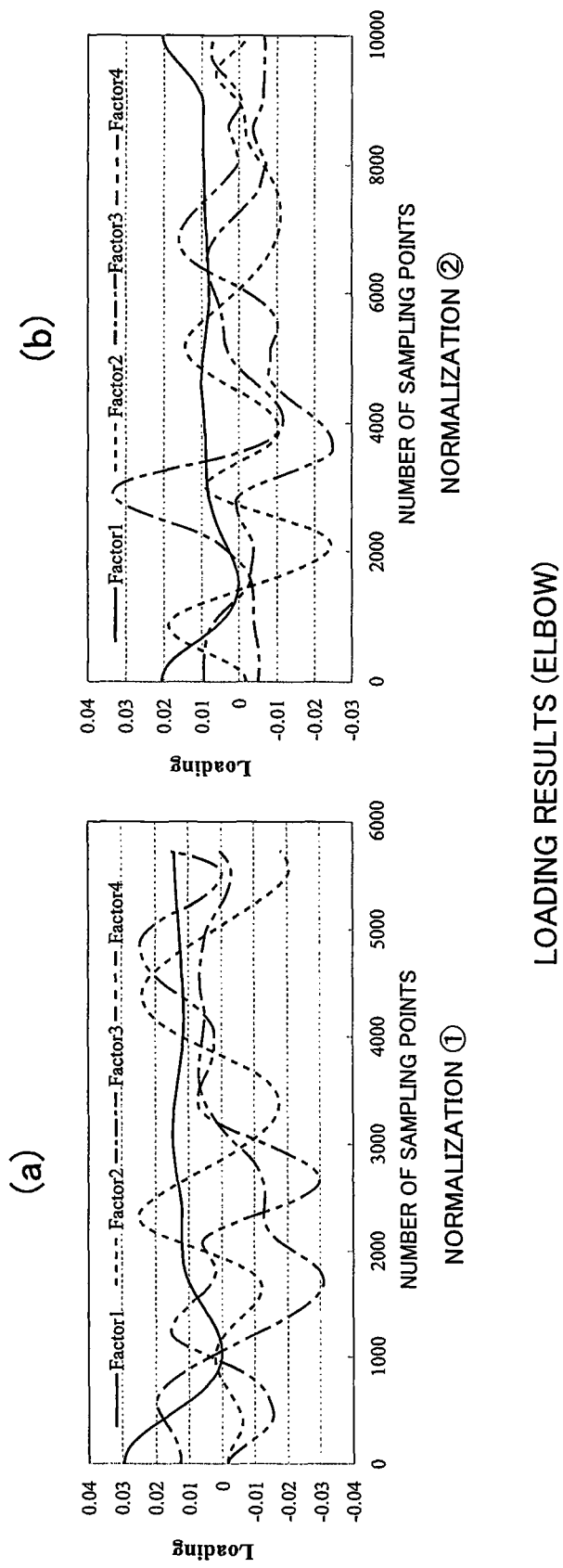
FIG. 6.4
LOADING RESULTS (ELBOW)

FIG. 7.1
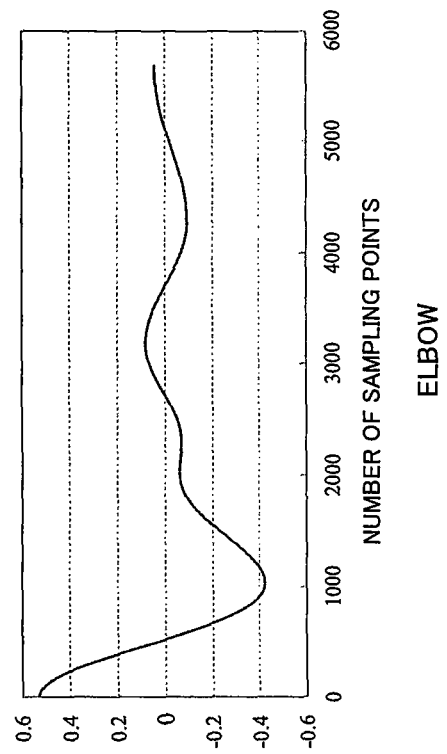
(b)
ELBOW
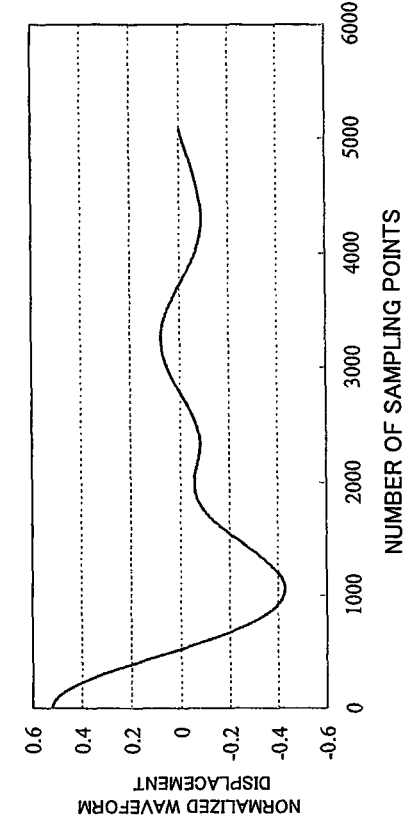
(a)
WRIST
ROW WAVEFORMS

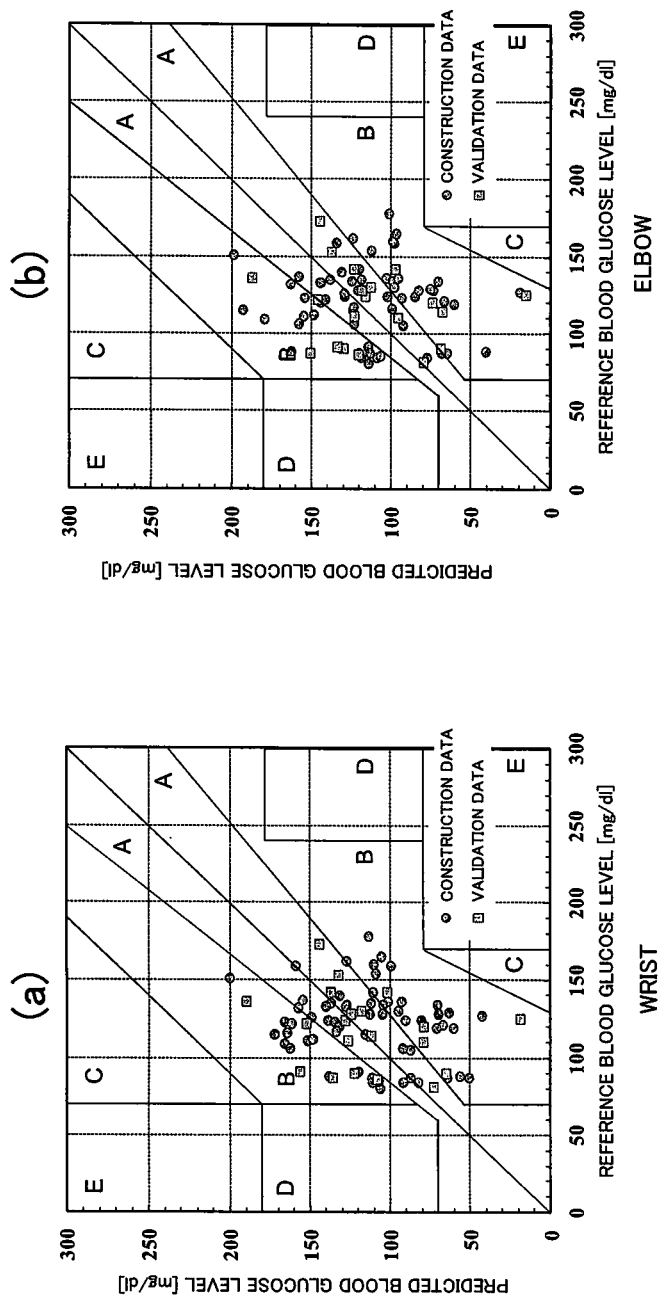
FIG. 7.2

FIG. 7.3

CALIBRATION CURVE CONSTRUCTION AND VALIDATION RESULTS (a) WRIST

| NUMBER OF CONSTRUCTION POINTS | AVERAGE VALUE | MINIMUM VALUE | MAXIMUM VALUE |
|---|---|---|---|
| 60 | 122 | 80 | 178 |

| PLS RESULTS | FACTOR NUMBER | CORRELATION COEFFICIENT | SEC [mg/dl] |
|---|---|---|---|
| | 4 | 0.21 | 40 |

| NUMBER OF VALIDATION POINTS | AVERAGE VALUE | MINIMUM VALUE | MAXIMUM VALUE |
|---|---|---|---|
| 20 | 118 | 81 | 173 |

| PLS RESULTS | SEP [mg/dl] |
|---|---|
| | 40 |

| EGA RESULTS | A zone | 45.0% (9/20) |
|---|---|---|
| | B zone | 55.0% (11/20) |

(b) ELBOW

| NUMBER OF CONSTRUCTION POINTS | AVERAGE VALUE | MINIMUM VALUE | MAXIMUM VALUE |
|---|---|---|---|
| 60 | 122 | 80 | 178 |

| PLS RESULTS | FACTOR NUMBER | CORRELATION COEFFICIENT | SEC [mg/dl] |
|---|---|---|---|
| | 4 | 0.09 | 43 |

| NUMBER OF VALIDATION POINTS | AVERAGE VALUE | MINIMUM VALUE | MAXIMUM VALUE |
|---|---|---|---|
| 20 | 118 | 81 | 173 |

| PLS RESULTS | SEP [mg/dl] |
|---|---|
| | 42 |

| EGA RESULTS | A zone | 45.0% (9/20) |
|---|---|---|
| | B zone | 55.0% (11/20) |

FIG. 7.4
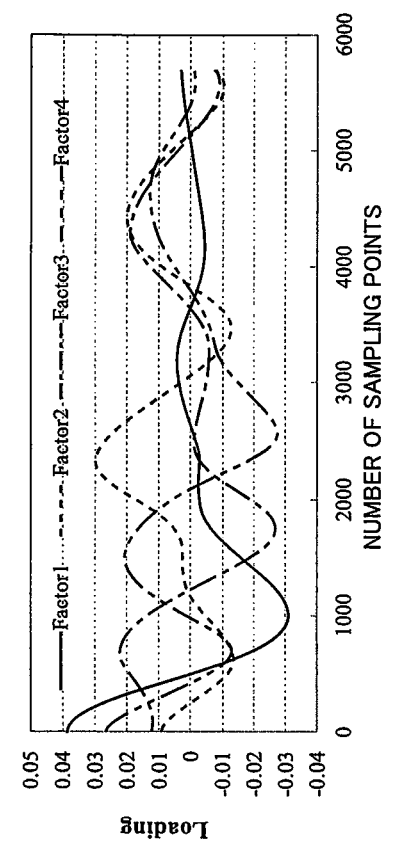
(a) WRIST
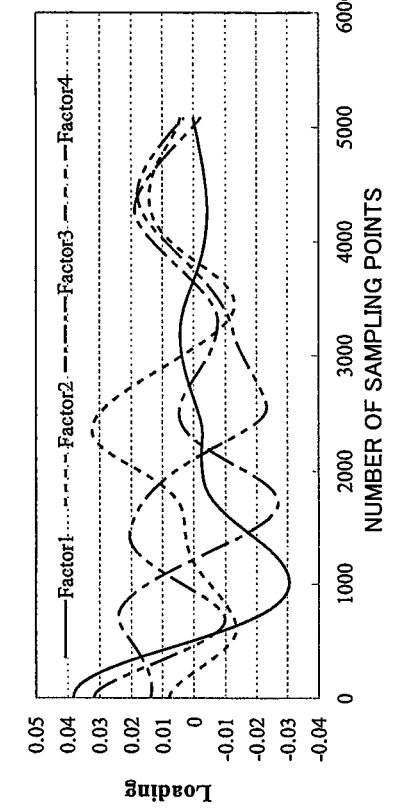
(b) ELBOW
LOADING RESULTS

NON-INVASIVE BLOOD GLUCOSE LEVEL MEASUREMENT METHOD AND NON-INVASIVE BLOOD GLUCOSE LEVEL MEASUREMENT DEVICE

TECHNICAL FIELD

The present invention relates to a non-invasive blood glucose level measurement method and device whereby the blood glucose level of a test subject can be measured utilizing an acceleration pulse wave measured from the test subject.

BACKGROUND ART

Measuring the blood glucose level is essential for preventing and treating diabetes. Measuring one's own blood glucose level (self-monitoring of blood glucose (SMBG)) has commonly been done by drawing blood through a needle, and measuring the blood glucose level with a blood glucose level sensor that uses the oxygen electrode method, etc. Such an invasive blood glucose level measurement method is a psychological burden to the test subject during the blood drawing. The economic burden from the disposal of needles, electrodes, and other materials also cannot be disregarded, and these materials are also one cause of increased medical expenses.

There have heretofore been advancements in research and development of non-invasive blood glucose level measurement methods to resolve the problems of invasive blood glucose level measurement methods. One such advancement is that non-invasive measurement methods using spectroscopic analysis have been examined. In Patent Document 1, the present inventor and others have proposed a biological information measurement device which measures blood glucose levels by spectroscopic analysis. In addition to optical techniques, systems have been proposed which account for the fluid-dynamic characteristics of blood to measure blood glucose levels, but such systems have not been put to practical use.

PRIOR ART DOCUMENTS

Patent Documents

Patent Document 1: JP 2012-191969 A

SUMMARY OF THE INVENTION

Problems to be Solved by the Invention

Conventionally proposed non-invasive blood glucose level measurement methods that use optical techniques, etc., sometimes do not stably meet practical requirements in terms of measurement accuracy. There are also many cases in which such methods do not meet practical requirements in terms of equipment costs.

An object of the present invention is to provide a non-invasive blood glucose level measurement method and device whereby blood glucose levels can be measured without using spectroscopic analysis.

Another object of the present invention is to provide a non-invasive blood glucose level measurement method and device having an inexpensive configuration whereby blood glucose levels can be measured with approximately the same measurement accuracy as invasive blood glucose level measurement methods.

Means of Solving the Problems

Focusing on the fact that a person's acceleration pulse wave, which can be observed by using a fiber Bragg grating sensor (referred to below as "FBG sensor") or other sensors, includes components that change depending on arterial blood density etc., the present inventors have discovered that blood glucose level information at the point in time of measurement can be extracted from waveform pattern characteristics of the measured acceleration pulse wave.

The non-invasive blood glucose level measurement method and device of the present invention, which were contrived on the basis of this discovery, are characterized in that an acceleration pulse wave of a test subject is measured, and blood glucose level information of the test subject is extracted from waveform information of the measured acceleration pulse wave, on the basis of a correlation between the blood glucose level measured by an invasive measurement method and the simultaneously-measured acceleration pulse wave.

Specifically, the non-invasive blood glucose level measurement method of the present invention is characterized by including a blood glucose level calculation step of finding, from waveform information regarding an acceleration pulse wave measured from a test subject, the blood glucose level when measurements were made of the acceleration pulse wave of the test subject, the blood glucose level being found on the basis of a predetermined correlation between the acceleration pulse wave and the blood glucose level, the correlation being established between a first blood glucose level, which is a blood glucose level measured with an invasive measurement method from the test subject or a different test subject, and a first acceleration pulse wave, which is an acceleration pulse wave measured at the same time that the first blood glucose level was measured.

The present inventor and others have confirmed that a calibration curve having a prescribed calibration precision can be created by performing a PLS (partial least squares) regression analysis, using a blood glucose level (a measurement value obtained by an invasive blood glucose self-measuring device complying with International Standard ISO 15197) found by an invasive measurement method (a direct measurement method) as an objective variable, and a simultaneously-measured acceleration pulse wave as an explanatory variable. The inventor et al. also confirmed that a prescribed blood glucose level prediction accuracy could be attained when validating the calibration curve as well. According to the measurement method of the present invention it is possible to achieve an inexpensively configured measurement device comprising an acceleration pulse wave measurement unit, and a data-processing unit for extracting blood glucose level information using a calibration curve that has been set in advance.

In the present invention, an acceleration pulse wave can be measured directly by using FBG sensors. The blood glucose level calculation step can be performed on the basis of a calibration curve constructed by performing a regression analysis, and particularly a calibration curve constructed by performing a PLS regression analysis, using a blood glucose level measured by an invasive measurement method as an objective variable, and a simultaneously-measured acceleration pulse wave as an explanatory variable.

In this case, it is preferable to use a normalized pulse wave of the first acceleration pulse wave as an explanatory variable for constructing the calibration curve, in order to increase the blood glucose level measurement accuracy. The waveform data of one pulse, obtained by performing waveform displacement normalization and waveform length normalization on the first acceleration pulse wave, can be used as the normalized pulse wave. Similarly, the acceleration pulse wave measured from the test subject in order to measure the blood glucose level is preferably normalized in the same manner.

The present inventor and others have confirmed that by performing a PLS regression analysis using a blood glucose level found by an invasive measurement method as an objective variable and a simultaneously-measured acceleration pulse wave as an explanatory variable, a calibration curve can be created with a blood glucose level range of 80 to 178 mg/dL and a calibration accuracy of ±15 mg/dL. The inventor and others have also confirmed that a similar blood glucose level prediction accuracy is attained also when validating the calibration curve.

It was also confirmed that with the use of FBG sensors, an acceleration pulse wave can be detected with a high time resolution of 20 kHz and a high sensitivity at the submicron level or lower, and the calibration curve accuracy exceeded that of conventional non-invasive measurement methods that use optical techniques. Furthermore, the factors of the detected calibration curve, which exhibit a significant contribution at the position where the propagation velocity of the acceleration pulse wave changes, are considered to be adequate.

According to the present invention, it is possible to achieve a non-invasive blood glucose level measurement method and device that can measure blood glucose levels through a novel technique that uses acceleration pulse waves. Additionally, according to the present invention, it is possible to achieve a non-invasive blood glucose level measurement method and device that can use acceleration pulse waves to measure blood glucose levels with approximately the same measurement accuracy as invasive blood glucose level measurement methods. Furthermore, according to the present invention, it is possible to achieve a non-invasive blood glucose level measurement method and device that use acceleration pulse waves and that are less expensive than conventional invasive blood glucose level measurement methods, and non-invasive blood glucose level measurement methods that use optical techniques, etc.

BRIEF DESCRIPTION OF THE DRAWINGS

FIG. 2.1 is a graph showing a pulse wave normalized by Normalization Method 1 of Experiment Example 1;

FIG. 2.2 is a graph showing the results of predicting blood glucose levels in the case of Normalization Method 1 of Experiment Example 1, and a chart showing the results of constructing and validating a calibration curve;

FIG. 2.3 is a graph showing loading results in the case of Normalization Method 1 of Experiment Example 1;

FIG. 2.4 is a graph showing a pulse wave normalized by Normalization Method 2 of Experiment Example 1;

FIG. 2.5 is a graph showing the results of predicting blood glucose levels in the case of Normalization Method 2 of Experiment Example 1, and a chart showing the results of constructing and validating a calibration curve;

FIG. 2.6 is a graph showing loading results in the case of Normalization Method 2 of Experiment Example 1;

FIG. 3.1 is a graph showing a sectioned waveform normalized by Normalization Method 1 in Experiment Example 2, and a graph showing a waveform with the length made uniform with the minimum number of sampling points;

FIG. 3.2 shows graphs showing the results of predicting blood glucose levels in the case of each of the waveforms of Experiment Example 2;

FIG. 3.3 is charts showing the results of constructing and validating a calibration curve in the case of each of the waveforms of Experiment Example 2;

FIG. 3.4 shows graphs showing the loading results in the case of each of the waveforms of Experiment Example 2;

FIG. 3.5 shows graphs showing waveforms normalized by Normalization Method 2 and sectioned at 5000 and 10000 sampling points in Experiment Example 2;

FIG. 3.6 shows graphs showing the results of predicting blood glucose levels in the case of each of the waveforms of Experiment Example 2;

FIG. 3.7 is charts showing the results of constructing and validating a calibration curve in the case of each of the waveforms of Experiment Example 2;

FIG. 3.8 shows graphs showing the loading results in the case of each of the waveforms of Experiment Example 2;

FIG. 4.1 is a graph showing a normalized pulse wave of the test subject of Experiment Example 3;

FIG. 4.2 shows graphs showing the results of predicting blood glucose levels in the case of Experiment Example 3;

FIG. 4.3 is a chart showing the results of constructing and validating a calibration curve in Experiment Example 3;

FIG. 4.4 is a graph showing loading results in Experiment Example 3;

FIG. 5.1 shows graphs showing three waveforms sectioned with different numbers of sampling points in Experiment Example 4;

FIG. 5.2 shows graphs showing the results of predicting blood glucose levels for each of the three waveforms sectioned with different numbers of sampling points in Experiment Example 4;

FIG. 5.3 is charts showing the results of constructing and validating a calibration curve for each of the three waveforms sectioned with different numbers of sampling points in Experiment Example 4;

FIG. 5.4 shows graphs showing the loading results for each of the three waveforms sectioned with different numbers of sampling points in Experiment Example 4;

FIG. 6.1 shows graphs showing the elbow waveforms normalized according to Normalization Methods 1 and 2 in Experiment Example 5;

FIG. 6.2 shows graphs showing the results of predicting blood glucose levels for both elbow waveforms normalized according to Normalization Methods 1 and 2 in Experiment Example 5;

FIG. 6.3 is charts showing the results of constructing and validating a calibration curve for both elbow waveforms normalized according to Normalization Methods 1 and 2 in Experiment Example 5;

FIG. 6.4 shows graphs showing the loading results for both elbow waveforms normalized according to Normalization Methods 1 and 2 in Experiment Example 5;

FIG. 7.1 shows raw waveforms of pulse waves of the wrist and elbow in Experiment Example 6;

FIG. 7.2 shows graphs showing the results of predicting blood glucose levels in both of these cases using raw waveforms in Experiment Example 6;

FIG. 7.3 is charts showing the results of constructing and validating a calibration curve in both of these cases using raw waveforms in Experiment Example 6; and FIG. 7.4 shows graphs showing loading results in both of these cases using raw waveforms in Experiment Example 6.

MODE FOR CARRYING OUT THE INVENTION

Figure 1:
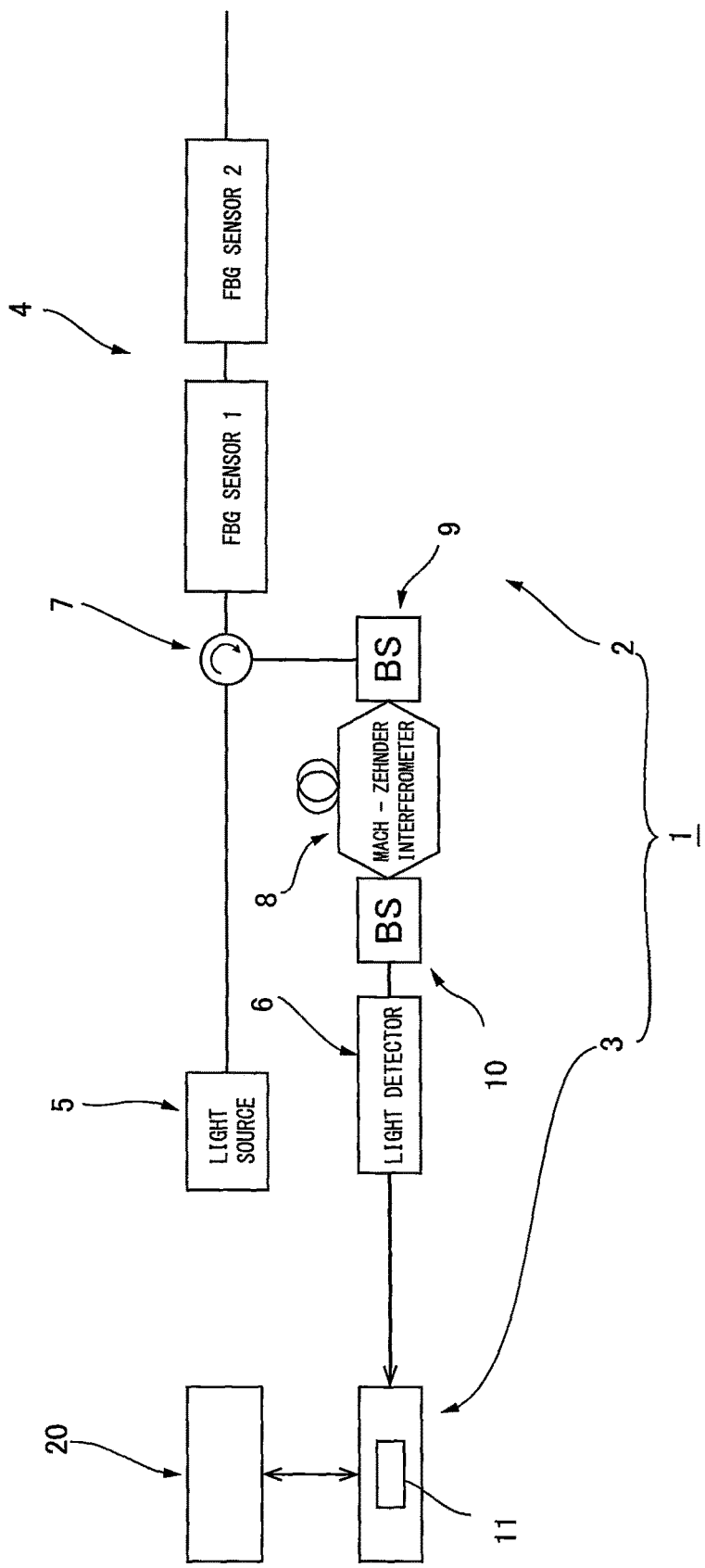
FIG. 1 is a schematic configuration view of a non-invasive blood glucose level measurement device according to an embodiment of the present invention.

Below is a description, made with reference to the drawings, of a non-invasive blood glucose level measurement device that uses acceleration pulse waves, to which the present invention is applied.

Summary of Measurement Device

FIG. 1 is a schematic configuration drawing of a non-invasive blood glucose level measurement device according to the present embodiment. The non-invasive blood glucose level measurement device 1 (referred to below as the "blood glucose level measurement device 1") has a pulse waveform measurement unit 2 for measuring an acceleration pulse wave of a test subject, a data-processing unit 3 for extracting blood glucose level information of the test subject from the waveform pattern characteristics of the measured acceleration pulse wave, and an operation/display unit 20. In the following description, the term "pulse wave" means an acceleration pulse wave unless otherwise specified.

The pulse waveform measurement unit 2 is provided with FBG sensors 4, a light source 5 for emitting a reference light impinging on the FBG sensors 4, and a light detector 6 for detecting the reflected light from the FBG sensors 4, the data-processing unit 3 calculating the blood glucose level of the test subject on the basis of the detection results of the light detector 6. The FBG sensors 4 are used after being attached to a location on the test subject where pulse waves are measured, e.g., the inside of the wrist, the inside of the elbow, etc.

The FBG sensors 4 include an FBG sensor 1 and an FBG sensor 2 in the present example, and reflected light from these sensors is guided to a Mach-Zehnder interferometer 8 via a circulator 7. Output light from the Mach-Zehnder interferometer 8 is detected by the light detector 6. The Mach-Zehnder interferometer 8 uses a beam splitter 9 on the incidence side to split the reflected light into two optical paths having an optical path difference, and superposes two optical paths that had been split by a beam splitter 10 on the output side into a single path, creating interfering light. Because coherent light has an interference fringe according to the optical path difference, the pattern of the interference fringe is measured, whereby the change in the Bragg wavelength occurring in the FBG sensors 4 is calculated, and the change in distortion, i.e., the pulse wave can be detected.

The elements of each part of the pulse waveform measurement unit 2 are presented below.

Light source 5: amplified spontaneous emission (ASE) light

FBG sensors 4:
  Bragg wavelength
    FBG sensor 1: 1550±0.5 nm
    FBG sensor 2: 1560±0.5 nm
  Length of FGB sensors 1, 2: 5 mm
  Fiber diameter: 145 μm
  Fiber core diameter: 10.5 μm
  Fiber material: silicon glass Light detector 6: InGaAs PIN PD
Wavelength resolution: ±0.1 μm The data-processing unit 3 is provided with a data-analyzing unit 11. Stored in advance in the data-analyzing unit 11 is a calibration curve, which is constructed by performing a PLS regression analysis, using the blood glucose level measured by an invasive measurement method (a direct measurement method) as an objective variable, and a simultaneously-measured acceleration pulse wave as an explanatory variable. On the basis of the calibration curve, the data-analyzing unit 11 predicts (estimates) the blood glucose level of the test subject from the acceleration pulse wave measured by the pulse waveform measurement unit 2. The configuration of the data-processing unit 3 is centered about a microcomputer, and the data-processing unit 3 functions as the data-analyzing unit 11 by executing a stored analysis program.

In the blood glucose level measurement device 1, the calibration curve is stored in the data-analyzing unit 11 in advance. As described above, the calibration curve is constructed by performing a PLS regression analysis, using the blood glucose level measured by an invasive measurement method as an objective variable, and a simultaneously-measured acceleration pulse wave as an explanatory variable. A calibration curve obtained in advance from the test subject whose blood glucose level is to be measured is used as the calibration curve. As an alternative, a calibration curve obtained in advance from another test subject can also be used.

When the blood glucose level is measured, for example, the test subject whose blood glucose level is to be measured is asked to lie still in a supine position so that the wrist, which is the measurement location, is at the same height as the heart. With the test subject in this position, medical tape, etc., is used to fix the FBG sensors 4 over the radial artery of one of the test subject's wrists, and an acceleration pulse wave is measured over a prescribed time period with a prescribed sampling cycle.

The measured acceleration pulse wave data is taken into the data-processing unit 3 and subjected to prescribed data processing. The data processing is the same as the processing performed on the acceleration pulse wave when the calibration curve is constructed.

For example, in the data-processing unit 3, first, the acceleration pulse wave is run through a band pass filter (not shown) having a prescribed passing band of, e.g., 0.5 to 5 Hz in order to remove noise. Next, after denoising, the acceleration pulse wave data is sectioned into one pulse using the peaks included in the acceleration pulse wave data as reference points, in order to separate the data into pulse wave portions of one pulse each. The multiple sectioned pieces of one-pulse acceleration pulse wave data are averaged to calculate the average pulse wave data for one pulse. The amplitude (waveform displacement) and length (number of sampling points) of this average pulse wave data are normalized.

In the data-analyzing unit 11 of the data-processing unit 3, the stored calibration curve is used to calculate the blood glucose level of the test subject at the time of the acceleration pulse wave measurement from the standardized average pulse wave data for one pulse. The calculated blood glucose level data is sent to, e.g., the operation/display unit 20 and is displayed on the display screen thereof.

In order to confirm the efficacy of the blood glucose level measurement method conducted using the blood glucose level measurement device 1, the inventors conducted various tests. Some of these tests are detailed below.

Experiment Example 1: First Analysis of Acceleration Pulse Wave of Wrist (Test Method and Analysis Method)

The FBG sensors 4 were attached with medical tape over the radial artery of the test subject's right wrist, and the test subject's pulse wave was measured. At the same time the pulse wave was measured, the test subject's blood glucose level was measured by a blood glucose meter ("FreeStyle Precision Pro," made by Abbott Japan Co., Ltd.), and the measured value was designated as a reference blood glucose level. The test subject was a male in his twenties, and the pulse wave measurement conditions were as follows.

Sampling frequency: 20 kHz
Measurement time: from start to end of measurement by automatic sphygmomanometer
Measurements taken: 80
Status/posture of test subject during measurement: lying supine, with measurement location held at same height as heart
While the measurements were taken, a band pass filter having a passing band of 0.5 to 5 Hz was used in order to remove noise. Additionally, the average pulse wave was used as described below in order to reduce noise due to body movement.

Specifically, using the peaks occurring in the pulse waves as reference points, the denoised pulse waves obtained in the measurements were sectioned for each pulse to obtain a plurality of one-pulse waves, which were averaged to create an average pulse wave for one pulse. Because eighty measurements were taken in the present example, eighty average pulse waves for one pulse were created.

Furthermore, errors were caused by differences in peak height and length among the average pulse waves obtained in the measurements; therefore, in order to remove these differences, a normalizing process was carried out on the average pulse waves as described below, and normalized average pulse waves were used.

Next, in order to analyze the correlation between the waveforms of the measured pulse waves (the waveforms of the average pulse waves after normalization) and the simultaneously-measured blood glucose levels, a regression model (calibration curve) was constructed by PLS regression analysis, using the reference blood glucose levels as objective variables and the pulse waves measured at the same time as the reference blood glucose levels as explanatory variables. A validation of the regression model was performed using a data set that was not used to construct the regression model. Sixty pieces of data were used to construct the regression model, and the remaining twenty were used to validate the regression model.

(Method of Normalizing Acceleration Pulse Wave)

Normalization of waveform displacement alone (Normalization Method 1), and normalization of both waveform displacement and number of sampling points (wavelength) (Normalization Method 2), were two methods used as the method of normalizing the pulse waves (average pulse waves).

Normalization Method 1: The value of pulse wave peaks was 1, and the minimum value was 0. Using the minimum number of sampling points of the eighty average pulse waves for one pulse obtained by the eighty measurements, the lengths of these pulse waves were made uniform.

Normalization Method 2: In addition to the aforementioned waveform displacement normalization, the pulse wave lengths were made uniform for 20000 sampling points.

(Test Results 1-1)

FIG. 2.1 is a graph showing the normalized waveform displacement of a normalized pulse wave (a normalized average pulse wave) obtained by normalizing a pulse wave through Normalization Method 1. FIG. 2.2($a$) is a graph showing the results of predicting blood glucose levels, and FIG. 2.2($b$) is an explanatory chart showing the results of constructing and validating a calibration curve. FIG. 2.3 is a graph showing loading results.

In the graph shown in FIG. 2.2($a$), construction data for the calibration curve, shown with circles, and validation data, shown with squares, are plotted on an error grid based on the error grid analysis method (EGA method). The horizontal axis of the error grid represents reference blood glucose levels, and the vertical axis represents predicted blood glucose levels.

The diagonal line represents conformity between the reference blood glucose levels and the predicted blood glucose levels. The plot being above the diagonal line represents an overestimation of the predicted blood glucose levels, and the plot being below the diagonal line represents an underestimation of the predicted blood glucose levels. The A zones in the error grid are areas where the predicted blood glucose levels deviate by only 20%. The sections of the A zones where the blood glucose level is lower than 70 mg/dL are areas indicating a low blood glucose level (<70 mg/dL). The B zones indicate areas where the predicted blood glucose levels deviate by more than 20% both above and below the reference blood glucose levels and benign medical treatment is performed. The C zones indicate areas where the preferred blood glucose levels are overcorrected. The D zones indicate areas where "dangerous failures" of detecting errors are committed, and the E zones indicate areas of "erroneous medical treatment."

(Test Results 1-2)

FIG. 2.4 is a graph showing the normalized waveform displacement of a normalized pulse wave obtained by normalizing a pulse wave through Normalization Method 2, FIG. 2.5($a$) is a graph showing the results of predicting blood glucose levels, and FIG. 2.5($b$) is an explanatory chart showing the results of constructing and validating a calibration curve. FIG. 2.6 is a graph showing loading results.

According to test results 1-1 and 1-2, blood glucose levels were predicted more accurately with Normalization Method 2 than with Normalization Method 1. According to FIGS. 2.3 and 2.6, the loading value increases at the falling of a peak of normalized waveform displacement, and at the rising of the second wave. Because a change in blood glucose level is one cause that affects blood viscosity, a change in blood glucose level is believed to affect the speed of a plethysmogram. Because the pulse waves measured by the FBG sensors 4 are acceleration pulse waves, the loading values are believed to be greater at the sloped sections of the acceleration pulse waves.

Experiment Example 2: Second Analysis of Acceleration Pulse Wave of Wrist (Test Method and Analysis Method)

The FBG sensors 4 were attached with medical tape over the radial artery of the right wrist of the same test subject as Experiment Example 1, and the pulse wave was measured. At the same time the pulse wave was measured, the blood glucose level was measured by a blood glucose meter ("FreeStyle Precision Pro," made by Abbott Japan Co., Ltd.), and the measured value was designated as a reference blood glucose level. The pulse wave measurement conditions were as follows.

Sampling frequency: 10 kHz
Measurement time: from start to end of measurement by automatic sphygmomanometer
Measurements taken: 80
Status/posture of test subject during measurement: lying supine, with measurement location held at same height as heart
While the measurements were taken, a band pass filter having a passing band of 0.5 to 5 Hz was used in order to remove noise. Additionally, the pulse waves obtained in the measurements were sectioned into waves of one pulse to obtain a plurality of one-pulse waves, which were averaged to create an average pulse wave.

In order to analyze the correlation between the waveform of the measured pulse wave (the average pulse wave) and the blood glucose level, a regression model (calibration curve) was constructed by PLS regression analysis, using the reference blood glucose levels as objective variables and the pulse waves measured at the same time as the reference blood glucose levels as explanatory variables. A validation of the regression model was performed using a data set that was not used to construct the regression model. Sixty items of data were used to construct the regression model, and the remaining twenty were used to validate the regression model.

(Methods of Normalizing and Sectioning Acceleration Pulse Waves)

Two methods of normalizing pulse waves were used: Normalization Method 1 (normalizing waveform displacement) and Normalization Method 2 (normalizing waveform displacement and number of sampling points).

Normalization Method 1: The value of pulse wave peaks was 1, and the minimum value was 0. Using the minimum number of sampling points, the lengths of these pulse waves were made uniform.

Normalization Method 2: In addition to normalizing waveform displacement, the pulse wave lengths were made uniform for 10000 sampling points.

In the method of sectioning pulse waves, a normalized waveform was sectioned at 5000 sampling points after the waveform was normalized as described above.

In the analysis, four types of waveforms were used: normalized waveforms obtained by normalizing with Normalization Method 1, one set being sectioned at 5000 sampling points, and one set of which the lengths were made uniform with the minimum number of sampling points; and normalized waveforms obtained by normalizing with Normalization Method 2, one set being sectioned at 5000 sampling points, and one set of which the lengths were made uniform with the 10000 sampling points.

(Test Results 2-1)

FIGS. 3.1(a) is a graph showing the normalized waveform displacement of a normalized pulse wave that has been normalized by Normalization Method 1 and sectioned at 5000 points, and FIG. 3.1(b) is a graph showing the normalized waveform displacement with the lengths made uniform with the minimum number of sampling points. FIGS. 3.2(a) and (b) are graphs showing the results of predicting blood glucose levels in each case, and FIGS. 3.3(a) and (b) are explanatory charts showing the results of constructing and validating a calibration curve in each case. FIGS. 3.4(a) and (b) are graphs showing the loading results in each case.

(Test Results 2-2)

FIGS. 3.5(a) is a graph showing a normalized pulse wave that has been normalized by Normalization Method 2 and sectioned at 5000 points, and FIG. 3.5(b) is a graph showing a normalized pulse wave with the lengths made uniform with 10000 sampling points. FIGS. 3.6(a) and (b) are graphs showing the results of predicting blood glucose levels in each case, and FIGS. 3.7(a) and (b) are explanatory charts showing the results of constructing and validating a calibration curve in each case. FIGS. 3.8(a) and (b) are graphs showing the loading results in each case.

Test results similar to the results of Experiment Example 1 were obtained. Specifically, according to test results 2-1 and 2-2, blood glucose levels were predicted more accurately with Normalization Method 2 than with Normalization Method 1.

Experiment Example 3: Third Analysis of Acceleration Pulse Wave of Wrist (Test Method and Analysis Method)

The test was conducted with a male test subject in his twenties, different from the test subject of Experiment Examples 1 and 2.

The FBG sensors 4 were attached with medical tape over the radial artery of the test subject's right wrist, and the pulse wave was measured. At the same time the pulse wave was measured, the blood glucose level was measured using a blood glucose meter ("FreeStyle Precision Exceed H," made by Abbott Japan Co., Ltd.), and the measured value was designated as a reference blood glucose level. The pulse wave measurement conditions were as follows.

Sampling frequency: 10 kHz
Measurement time: 15 seconds from start of measurement by automatic sphygmomanometer
Measurements taken: Sixty
Status/posture of test subject during measurement: lying supine, with measurement location held at same height as heart The measured pulse waves were passed through a band pass filter having a passing band of 0.5 to 5 Hz in order to remove noise. Additionally, the denoised pulse waves were sectioned into single pulses, using the peaks as reference points. In order to reduce noise due to body movement, the sectioned one-pulse waves were averaged. Because the average pulse rate of a common adult is 60 bpm, approximately fifteen one-pulse waves were sectioned with a single measurement. These pulse waves were averaged to calculate the average of sixty pulse waves.

Because errors are caused by differences in peak height and length among the pulse waves, the average pulse wave was subjected to both normalization of waveform displacement in which the value of the initial point (peak) of the average pulse wave was 1 and the minimum value was 0, and normalization of length in which the number of samples was 10000, similar to Normalization Method 2 in Experiment Examples 1 and 2.

A calibration curve was constructed with PLS regression analysis, using the normalized pulse waves obtained by normalization as explanatory variables and reference blood glucose levels as objective variables, and blood glucose levels were calculated.

(Test Results)

FIG. 4.1 shows a normalized pulse wave of the test subject, FIG. 4.2 shows the blood glucose level calculation results, FIG. 4.3 shows the results of constructing and validating a calibration curve in a table, and FIG. 4.4 shows the loading results for a PLS regression analysis. According to FIGS. 4.2 and 4.3, the correlation was high, the SEP and SEC were both small, and the validation results all stayed within the A zones.

Experiment Example 4: Examination of Sectioning Positions of Acceleration Pulse Wave According to the loading results of Experiment Examples 1, 2, and 3 (FIGS. 2.3, 2.6, 3.4, 3.8, 4.4), with either test subject so far, the loading value is larger in the first half of the normalized pulse wave up to a sampling point number of 6000. Therefore, the first half of the normalized pulse wave is believed to be effective for blood glucose level measurement.

An analysis was performed with different sectioned positions of the pulse wave in order to confirm the sections that were effective for blood glucose level prediction from loading. The pulse wave used in this case was the waveform of a normalized pulse wave normalized by Normalization Method 2 in the wrist, and the sampling frequency was 20 kHz. The pulse wave was sectioned at three different positions, where the number of sampling points was 10000, 15000, and 19000. The measurement conditions were otherwise the same as those of Experiment Example 1.

FIGS. 5.1(a), (b), and (c) show the normalized pulse waves after sectioning, FIGS. 5.2(a), (b), and (c) show the results of predicting blood glucose levels in each of these cases, FIGS. 5.3(a), (b), and (c) show the results of constructing and validating a calibration curve in each of these cases, and FIGS. 5.4(a), (b), and (c) show the loading results in each of these cases.

In each of these cases, a high correlation was confirmed between the normalized pulse wave and the blood glucose level, and it was confirmed that blood glucose levels could be predicted with a high accuracy. It is believed that the blood glucose level can be predicted with a higher accuracy by sectioning the normalized pulse wave so as to include a section up to a sampling point number of 6000, which is the first half of the normalized pulse wave.

Experiment Example 5: Analysis of Acceleration Pulse Wave of Elbow

In Experiment Examples 1, 2, and 3, analysis was performed using the pulse wave of the wrist. In order to confirm the validity of the blood glucose level measurement using a pulse wave measured in a location other than the wrist, in this test, the pulse wave of the elbow was measured with the same test subject as Experiment Examples 1 and 2, and the same analysis was performed using the measured pulse wave.

Similar to the case of the wrist, two methods were employed as the normalization methods: normalization of waveform displacement (Normalization Method 1), and normalization of both waveform displacement and number of sampling points (Normalization Method 2). The sampling frequency in the measurements was 10 kHz. The measurement conditions were otherwise the same as those of Experiment Example 1.

FIGS. 6.1(a) and (b) show the respective waveforms normalized by Normalization Methods 1 and 2, FIGS. 6.2(a) and (b) show the results of predicting blood glucose levels in both of these cases, FIGS. 6.3(a) and (b) show the results of constructing and validating a calibration curve in both of these cases, and FIGS. 6.4(a) and (b) show the loading results in both of these cases.

It was confirmed that there was a prescribed correlation with the blood glucose level even when using a normalized pulse wave of a pulse wave measured at the elbow. The blood glucose level could also be predicted more accurately with Normalization Method 2 than with Normalization Method 1.

Experiment Example 6: Analysis of Raw Waveforms of Wrist and Elbow

In order to confirm that normalizing the measured pulse wave was effective for improving the accuracy of the blood glucose level measurement, in this example, blood glucose level measurements were taken using a raw waveform of the measured acceleration pulse wave.

Specifically, in this example, pulse waves were measured at both the wrist and the elbow in the same manner as in Experiment Examples 1 and 2. Analysis was performed using a raw waveform, in which normalization had not been performed on the pulse waves measured at the wrist and elbow. The sampling frequency was 10 kHz. The measurement conditions were otherwise the same as those of Experiment Example 1.

FIGS. 7.1(a) and (b) show raw waveforms of pulse waves of the wrist and elbow. FIGS. 7.2(a) and (b) are graphs showing the results of predicting blood glucose levels in both of these cases. FIGS. 7.3(a) and (b) are charts showing the results of constructing and validating a calibration curve in both of these cases. FIGS. 7.4(a) and (b) are graphs showing loading results in both of these cases. It was confirmed that using a normalized pulse wave of a measured pulse wave is more effective than using a calibration curve obtained from a raw waveform.

Versatility of Blood Glucose Level Measurement Method Using Acceleration Pulse Wave For the Experiment Example described above, a calibration curve for the same test subject was constructed and validated. It is also possible to construct a calibration curve for calculating the blood glucose level for one test subject, and to use this constructed calibration curve to the measure blood glucose level from a pulse wave of another test subject. The blood glucose level can be measured with a prescribed accuracy in this case as well.

Other Embodiments (Pulse Wave Sensor)

The blood glucose level measurement device 1 described above measures pulse waves using FBG sensors 4. An acceleration pulse wave can also be measured directly using pulse wave sensors other than FBG sensors. It is also possible to measure a plethysmogram and calculate the secondary derivative of the measured pulse wave to find the acceleration pulse wave, and to use this acceleration pulse wave as a basis to measure the blood glucose level.

There are four conventionally known types of pulse wave sensors: photoelectric, mechanical, impedance, and strain gauge. While any of these sensors can be used, it is preferable to use a sensor that can detect pulse waves accurately. Examples that can be used include a high-sensitivity pressure sensor (L-series sensor, made by EMFit Ltd., Finland), a tactile sensor (T4000/6000 series, made by Pressure Profile Systems, U.S.A.), etc.

(Method of Calculating Correlation Between Acceleration Pulse Wave and Blood Glucose Level)

In the above embodiments, PLS regression analysis is used as the regression analysis method. Another regression analysis method can also be used to find the correlation between blood glucose level measured by invasive measurement and a simultaneously-measured acceleration pulse wave.

(Pulse Wave Measurement Location)

In the above Experiment Examples, the pulse wave is measured at the wrist and elbow. Other locations may be used as the locations for measuring the pulse wave.

The invention claimed is:
1. A non-invasive blood glucose level measurement method comprising the steps of:

measuring a first acceleration pulse wave from a test subject with an acceleration pulse wave measurement unit to obtain a measured first acceleration pulse wave and a first blood glucose level with an invasive measurement device to obtain a measured first blood glucose level;

constructing a calibration curve based on a correlation between the measured first acceleration pulse wave and the measured first blood glucose level;

storing the calibration curve in a data-analyzing unit;

measuring a second acceleration pulse wave with the acceleration pulse wave measurement unit to obtain a measured second acceleration pulse wave;

introducing the measured second acceleration pulse wave into the data-analyzing unit; and calculating a second blood glucose level utilizing the stored calibration curve.

2. The non-invasive blood glucose level measurement method according to claim 1, wherein the correlation is defined by a calibration curve constructed by performing a partial least squares regression analysis, using the measured first blood glucose level as an objective variable, and the measured first acceleration pulse wave as an explanatory variable.

3. The non-invasive blood glucose level measurement method according to claim 2, wherein a first normalized pulse wave of the measured first acceleration pulse wave is used as the explanatory variable for constructing the calibration curve, and wherein the first normalized pulse wave is waveform data of one pulse, the waveform data being obtained by performing waveform displacement normalization and waveform length normalization on the measured first acceleration pulse wave.

4. The non-invasive blood glucose measurement method according to claim 1, further including:

a measurement step of measuring the first acceleration pulse wave from the test subject by using a fiber Bragg grating sensor, wherein in the blood glucose level calculation step, the blood glucose level is obtained by using a normalized pulse wave of the first acceleration pulse wave that was measured from the test subject and the normalized pulse wave is waveform data of one pulse, the waveform data being obtained by performing waveform displacement normalization and waveform length normalization on the measured first acceleration pulse wave.

5. A non-invasive blood glucose level measurement device comprising:

a pulse waveform measurement unit for measuring an acceleration pulse wave of a test subject;

a storing part for storing a prescribed correlation between acceleration pulse waves and blood glucose levels; and a data-processing unit for calculating a blood glucose level of the test subject by using a correlation based on waveform data of a measured first acceleration pulse wave and a measured first blood glucose level, wherein the correlation is established between a first blood glucose level that is a blood glucose level measured with an invasive measurement method from the test subject or a different test subject and a first acceleration pulse wave that is an acceleration pulse wave measured at the same time that the first blood glucose level was measured.

6. The non-invasive blood glucose level measurement device according to claim 5, wherein the pulse waveform measurement unit has a fiber Bragg grating sensor.

7. The non-invasive blood glucose level measurement device according to claim 5, wherein the correlation is defined by a calibration curve constructed by performing a partial least squares regression analysis, using the measured first blood glucose level as an objective variable, and the measured first acceleration pulse wave as an explanatory variable, and the data-processing unit has a data-analyzing unit for calculating the blood glucose level by using the calibration curve.

8. The non-invasive blood glucose measurement device according to claim 7, wherein the data-analyzing unit calculates the blood glucose level from the calibration curve by using a normalized pulse wave of the measured first acceleration pulse wave measured by the pulse waveform measurement unit and the normalized pulse wave is waveform data of one pulse, the waveform data being obtained by performing waveform displacement normalization and waveform length normalization on the measured first acceleration pulse wave.

* * * * *